(12) United States Patent
Robertson et al.

(10) Patent No.: US 7,205,117 B1
(45) Date of Patent: Apr. 17, 2007

(54) CANCER DETECTION METHOD AND REAGENTS

(75) Inventors: John Forsyth Russell Robertson, Nottingham (GB); Catherine Rosemund Graves, Nottingham (GB); Michael Rawling Price, Nottingham (GB); Frances Margaret Price, Nottingham (GB)

(73) Assignee: University of Nottingham, Nottingham (GB)

( * ) Notice: Subject to any disclaimer, the term of this patent is extended or adjusted under 35 U.S.C. 154(b) by 45 days.

(21) Appl. No.: 09/857,739

(22) Filed: Jun. 8, 2001

Related U.S. Application Data

(63) Continuation of application No. PCT/GB99/04182, filed on Dec. 10, 1999.

(30) Foreign Application Priority Data

Dec. 10, 1998 (GB) .................................. 9827228.9

(51) Int. Cl.
*G01N 33/53* (2006.01)
(52) U.S. Cl. ...................... 435/7.23; 436/501; 436/518
(58) Field of Classification Search ............... 435/7.23, 435/7.1; 436/506, 64
See application file for complete search history.

(56) References Cited

U.S. PATENT DOCUMENTS

| | | | |
|---|---|---|---|
| 4,898,951 A | 2/1990 | Symons | |
| 4,937,185 A | 6/1990 | Webb et al. | |
| 5,157,020 A * | 10/1992 | Kay et al. ...................... | 514/13 |
| 5,652,115 A | 7/1997 | Marks et al. | |
| 5,726,023 A | 3/1998 | Cheever et al. | |
| 5,876,728 A | 3/1999 | Kass et al. | |
| 6,322,989 B1 | 11/2001 | Cohen | |

FOREIGN PATENT DOCUMENTS

| | | |
|---|---|---|
| EP | 0 236 606 | 6/1992 |
| JP | 09 189702 | 7/1997 |
| WO | WO 92/13065 | 8/1992 |
| WO | WO 93/11236 | 6/1993 |
| WO | WO 93/21529 | 10/1993 |
| WO | WO 94/23728 | 10/1994 |
| WO | WO 96/00084 | 1/1996 |
| WO | WO 96/03502 A2 | 2/1996 |
| WO | WO 97/14794 | 4/1997 |
| WO | WO 99/58978 A2 | 11/1999 |
| WO | WO 00/26668 | 5/2000 |

OTHER PUBLICATIONS von Mensdorff-Pouilly et al, Eur J Cancer. Jul. 1996;32A(8):1325-31.*
Gourevitch et al, Br J Cancer. Oct. 1995;72(4):934-8.*
Petrarca et al, Eur J Cancer. Nov. 1996;32A(12):2155-63.*
Definition of "moncyte" in On-line Medical Dictionary downloaded on Feb. 5, 2005 from url..cnacerweb.ncl.ac.uk.*
Voet et al., (1990, Biochemistry, pp. 1096, and 1098 only).*
Voet et al., (1990, Biochemistry, p. 78 only).*
Janeway et al., (Immunobiology downloaded from url.ncbi.nlm.nih.gov/books, total 2 pages).*
Rao, S.G., "Detection of Human Ovarian Tumor Associated Antigens by Autologous Antibodies Isolated from Ovarian Carcinoma Ascites Fluid"; *Proceedings of the American Association for Cancer Research Annual Meeting*, 1987, vol. 28, p. 358.
Fishman, P., "Application of autoantibodies to cancer therapy: A new concept", *The 9th International Congress of Immunology*, 1995, p. 664.
Kutteh, W.H., et al., "Immunologic characterization of tumor markers in human ovarian cancer cell lines"; *Journal of the Society for Gynecologic Investigation*, 1996, vol. 3, No. 4, pp. 216-222.
Houghton et al.; "Detection of Cell Surface and Intracellular Antigens by Human Monoclonal Antibodies—Hybrid Cell Lines Derived from Lymphocytes of Patients with Malignant Melanoma*"; *J. Exp. Med.*; vol. 158, Jul. 1983; pp. 53-65.
Rao et al.; "Detection of human ovarian tumor-associated antigens by antibodies isolated from ovarian carcinoma ascitic fluid"; *Am J Obstet Gynecol*; Jul. 1988; vol. 159, No. 1; pp. 94-98.
Petrarca, C., "Human Antibodies Against the Polymorphic Epithelial Mucin in Ovarian Cancer Patients Recognise a Novel Sequence in the Tandem Repeat Region"; *European Journal of Cancer*, vol. 32A, No. 12, pp. 2155-2163, 1996.
Von Mensdorff-Pouilly, S., "Humoral Immune Response to Polymorphic Epithelial Mucin (MUC-1) inpatients with Benign and Matignant Breat Tumours"; *European Journal of Cancer*, vol. 32A, No. 8, pp. 1325-1331, 1996.
Gourevitch, MM; "Polymorphic epithelial mucin (MUC-1)-containing circulating immune complexes in carcinoma patients"; *British Journal of Cancer*, 72, pp. 934-938; (1995).
Sahin et al.; PNAS, 1995, vol. 92, pp. 11810-11813.
Scanlan et al.; International Journal of Cancer, 1998, vol. 76, pp. 652-658.
Petrakou et al.; International Journal of oncology, 1997, vol. 11, suppl. p. 902.
Koterra et al.; Caner Research, 1994, vol. 54, pp. 2856-2860.
Abstract of Mensdorf-Pouilly et al.; Anticancer Research, Nov.-Dec. 1997, vol. 17, p. 4184.
Denton et al.; Cancer Letters, 1993, vol. 70, pp. 143-150.
Zisman et al.; Journal of Urology, 1995, vol. 154, pp. 1052-1055.
Deguchi et al.; Int. Arch. Allergy Appl. Immunol., 1988, vol. 87, pp. 313-316.

(Continued)

*Primary Examiner*—Misook Yu
(74) *Attorney, Agent, or Firm*—Kilpatrick Stockton LLP

(57) ABSTRACT

Sensitive and specific methods are provided for use in detecting the presence of cancer marker proteins in the body fluids of a mammal. Also provided are autoantibodies for use in these methods and immortalized cells, which are a source of the autoantibodies.

18 Claims, 8 Drawing Sheets

OTHER PUBLICATIONS

Abstract of Yamamoto et al.; Proc. Amer. Soc. Cancer Res., Mar. 1997, p. 564.
Disis et al.; Journal of Clinical Oncology, 1997, vol. 15, pp. 3363-3367.
Croce et al.; Cancer. Immunol. Immunother., 1995, vol. 40, pp. 132-137.
Green et al.; European Journal of Cancer, 1994, vol. 30A, pp. 580-584.
Stearns et al.; Breast Cancer Research and Treatment, Feb. 8, 1998, vol. 52, pp. 239-259.
Kawahara; Cancer, 1986, vol. 58, pp. 2008-2012.
Abstract of Hayes; Anticancer Drugs, 1995, vol. 6, suppl. 2, pp. 26-27.
Abstract of Pandha et al.; Cancer Gene Therapy, 1997, vol. 4, No. 5, p. 310.
Bhatti et al.; Journal of Tumor Marker Oncology, Summer-1994, vol. 9, pp. 125-131.
Aparecida et al., "Value of CEA Level Determination in Gallbladder Bile in the Diagnosis of Liver Metastases Secondary to Colorectal Adenocarcinoma", Sao Paulo Medical Journal, 2001, vol. 119, No. 3, pp. 110-113.
Apostolopoulos et al., Nature Medicine, 1998, vol. 4, pp. 315-320.
Baechstrom, et al., "Purification and Characterization of Sialyl-Le—Carrying Mucins of Human Bile; Evidence for the Presence of MUC1 and MUC3 Apoproteins", The Journal of Biological Chemistry, 1994, vol. 269, No. 20, pp. 14430-14437.
Beatty, et al., "Biochemical Characterization of the Soluble Form of Tumor Antigen MUC1 Isolated from Sera and Ascites Fluid of Breast and Pancreatic Cancer Patients", Clinical Cancer Research, 2001, vol. 7, pp. 781-787.
Hill et al., "Nature of Carcinoembryonic Antigen Purified From Malignant Ascitic Fluid of Serous Cystadenocarcinoma of the Ovary", Molecular Immunology, 1981, vol. 18, No. 7, pp. 647-653.
Karanikas, et al. J Clin Invest Dec. 1, 1997, vol. 100, No. 11, pp. 2783-2792.
Kuralay, et al., Diagnostic Usefulness of Tumour Marker Levels in Pleural Effusions of Malignant and Benign Origin, Clinica Chimica Acta, 2000, vol. 300, pp. 43-55.
Lafond, R.E., et al., "Autoantibodies to c-myc protein: elevated levels in patients with African Burkitt's lymphoma and normal Ghanians", *Autoimmunity*, vol. 13, No. 3, 1992, pp. 215-224.
Lai, et al., "Presence of Serum Anti-P53 Antibodies is Associated with Pleural Effusions and Poor Prognosis in Lung Cancer Patients", Clinical Cancer Research, 1998, vol. 4, pp. 3025-3030.
Lawniczak, et al., "The Search for Tumor-Associated Proteins in Pleural Effusions by Means of Monoclonal Antibodies and a Dot Blot Assay", Lung, 1992, vol. 170, pp. 65-74.
Montenarh, et al., "P53 Autoantibodies in the Sera, Cyst and Ascitic Fluids of Patients with Ovarian Cancer", International Journal of Oncology, 1998, vol. 13, pp. 605-610.
Nery, et al., "Isolation and Partial Characterization of Macromolecular Urinary Aggregates Containing Carcinoembryonic Antigen-Like Activity", Br J. Cancer, 1974, vol. 29, No. 413.
Nustad et al., "Epitopes on CA 125 from Cervical Mucus and Ascites Fluid and Characterization of Six New Antibodies", pp. 303-314.
Pavelic et al., Anticancer Reasearch, 1991, vol. 11, pp. 1421-1428.
Rusciano, "Concomitant Purification of Prostatic Carcinoma Tumor Markers from Human Seminal Fluid Under Nondenaturing Conditions", Clinical Chemistry, 1988, vol. 34, No. 12, pp. 2528-2532.
Sandrin et al., Glycoconjugate Journal, 1997, vol. 14, pp. 97-105.
Schneider, J. "P53 Protein, EGF Receptor, and Anti-P53 Antibodies in Serum from Patients with Occupationally Derived Lung Cancer", British Journal of Cancer, 1999, vol. 80, No. 12, pp. 1987-1994.
Shibata, et al., "Purification and Characterization of Prostate Specific Antigen from Human Urine", Biochimica et Biophysica Acta, 1997, vol. 1336, pp. 425-433.
Sokoloff, et al., "A Dual-Monoclonal Sandwich Assay for Prostate-Specific Membrane Antigen: Levels in Tissues, Seminal Fluid and Urine", The Prostate, 2000, vol. 43, pp. 150-157.
Stubbs, et al., "Faecal Carcinoembryonic Antigen (CEA) in Patients with Large Bowel Cancer", European Journal of Surgical Oncology, 1987, vol. 13, pp. 433-436.
Tondini, et al., "Comparison of CA15-3 and Carcinoembryonic Antigen in Monitoring the Clinical Course of Patients with Metastatic Breast Cancer", Cancer Research, 1988, vol. 48, No. 14, pp. 4107-4112.
Toth, et al., "A Carcinoembryonic Antigen (CEA) Binding Protein From Ascites Influences CEA Uptake by Macrophages", 1990, vol. 171, No. 2, pp. 633-640.
Venegas, et al., "Purification and Immunochemical Characterization of Ascitic Fluid Glycoproteins Containing Certain Tumor-Associated and Blood Group Antigen Markers", Glycoconjugate Journal, 1989, vol. 6, pp. 511-524.
Volkmann, M., et al., "Anti-p53 autoantibodies as serological marker in different tumor-entities", *Clinical Chemistry*, vol. 41, No. S6 part 2, 1995, pp. S221-S222.
Wolf, et al., "A Tumour-Associated Antigen from The Pleural Effusion of Patients with Squamous-Cell Carcinoma of Lung", Br. J. Cancer, 1978, vol. 36, pp. 1046-1052.
Yamamoto et al., "L-Myc Overexpression and Detection of Auto-Antibodies Against L-Myc in Both the Serum and Pleural Effusion from a Patient with Non-Small Cell Lung Cancer", Internal Medicine, 1997, vol. 36, No. 10, pp. 724-727.
Güre, "Human Lung Cancer Antigens Recognized by Autologous Antibodies Definition of a Novel cDNA Derived from the Tumor Suppressor Gene Locus on Chromosome 3p21.3", Ludwig Institute for Cancer Research, pp. 1034-1040, 1998, Cancer Res, vol. 58.
Hinoda, et al., "Detection of a Circulating Antibody Against a Peptide Epitope on a Mucin Core Protein, MUC1, in Ulcerative Colitis", 1991, pp. 163-168.
Laeng, et al., "Anti-Neural Autoantibodies, types 1 and 2: Their Utility in the Study of Tumors of the Nervous System", Acta Neuropathol, 1998, vol. 96, pp. 329-339.
Luo, et al., "Identification of Heat Shock Protein 90 and Other Proteins as Tumour Antigens by Serological Screening of an Ovarian Carcinoma Expression Library", British Journal of Cancer, 2002, vol. 87, pp. 339-343.
Mercer, "Use of Multiple Markers to Enhance Clinical Utility", Immunology Series, vol. 53, 1990, pp. 39-54.
Yamauchi, et al., "Autoantibodies to C-MYC Nuclear Protein Products in Autoimmune Disease", 1989, pp. 117-119.

* cited by examiner

FIG. 4

TAPPAHGVT*SAPDTRPAPGST*APPA

T* are O-glycosilated with N-acetyl-galactosamine

SANDWICH ELISAs PERFORMED ON NORMAL AND CANCER SAMPLES

SEQUENCE LISTING

<160> NUMBER OF SEQ ID NOS: 1

<210> SEQ ID NO 1

-continued

```
<211> LENGTH: 25
<212> TYPE: PRT
<213> ORGANISM: Artificial Sequence
<220> FEATURE:
<223> OTHER INFORMATION: Synthetic MUC1 peptide TAP2
<220> FEATURE:
<221> NAME/KEY: MISC_FEATURE
<222> LOCATION: (9)..(9)
<223> OTHER INFORMATION: T is O-glycosylated with N-acetyl-galactosamine
<220> FEATURE:
<221> NAME/KEY: MISC_FEATURE
<222> LOCATION: (21)..(21)
<223> OTHER INFORMATION: T is O-glycosylated with N-acetyl-galactosamine

<400> SEQUENCE: 1

Thr Ala Pro Pro Ala His Gly Val Thr Ser Ala Pro Asp Thr Arg Pro
1               5                   10                  15

Ala Pro Gly Ser Thr Ala Pro Pro Ala
            20                  25
```

CANCER DETECTION METHOD AND REAGENTS

RELATED APPLICATIONS

This application is continuation of a national stage filing 35 U.S.C. §120 or 35 U.S.C. §365(c) of PCT International application PCT/GB99/04182 designating the United States of America, and filed Dec. 10, 1999, was published under PCT Article 21(2) in English.

Foreign priority benefits are claimed under 35 U.S.C. §119(a)–(d) or 35 U.S.C. §365(b) of British application number 9827228.9 filed Dec. 10, 1998, which designated at least one country other than the United States.

The present invention relates to highly sensitive and specific methods for detecting the presence of cancer marker proteins in the bodily fluids of a mammal, to autoantibodies for use in these methods, to immortalised cells for obtaining these autoantibodies and to kits for performing the methods. These methods are useful in the early detection of carcinogenic or pre-neoplastic modifications in asymptomatic patients, in monitoring the progress of cancer, in screening for recurrence of the disease in patients who have previously undergone anti-cancer treatment, in monitoring the efficacy of a systematic treatment in a patient and in determining the most appropriate treatment for a particular patient.

Cancer and pre-neoplastic cells are characterised by the production of cancer-associated marker proteins. These often consist of aberrant forms of wild-type proteins, which are produced by cancer cells as a result of genetic mutations or altered post-translational processing. Alternatively, cancer markers can also be proteins that become over-expressed in tumour cells, usually as a result of gene amplification or abnormal transcriptional regulation. In some cases, these two phenomena may occur at the same time leading to an accumulation of modified proteins throughout the development of the disease. For example, modified forms of Ras, p53, c-myc, MUC-1, c-erbβ2 have been found to be associated with a wide variety of cancers.

Cancer associated proteins are found both in the tissues and in the bodily fluids of an individual who carries pre-neoplastic or cancer cells. Their levels are very low at the early stages of the carcinogenic process and increases during progression of the disease. The detection of these proteins has advantageously been used in routine tests for the diagnosis of cancer but, unfortunately, these assays have many limitations. In particular, commercial antibodies available for use in standard tests are usually not sensitive enough to detect the low levels of cancer-associated proteins that are found at the very early stages of the disease, for example in asymptomatic patients, when a treatment would be the most effective. In addition, most commercial antibodies are not specific for modified forms of cancer-associated markers and cross-react with wild-type forms of these proteins. As a consequence, they are only useful for detecting substantial increases in serum levels of cancer marker proteins, which usually occur at advanced stages of cancer.

For example, the commercial assay CA15-3, which detects both unmodified and modified forms of MUC1, is useful in the diagnosis of metastatic breast cancers, which are characterised by elevated serum levels of MUC1. However, this assay cannot be used in screening for neoplasia or primary breast cancer because the serum levels of MUC1 at these stages do not differ significantly from those in normal individuals (Robertson et al. (1990), Eur. J. Cancer 26: 1127–1132). Other marker proteins such as, for example, carcinoembryonic antigen (CEA) and the marker CA19.9 have been reported to be elevated in the serum of patients with metastatic breast and colorectal cancer but not that of patients with primary cancers (Robertson et al. (1991), Cancer Immunol. Immunother. 133: 403–410; Thomas et al. (1991) Br. J. Cancer 63: 975–976). Also in the case of these cancer markers, available commercial assays are not able to discriminate between modified and wild-type forms of the proteins and are therefore of limited use. Furthermore, commercially available antibodies, by cross-reacting with normal forms of cancer-associated proteins, may also lead to false positive results. Thus, there is a need in the art for more sensitive and specific antibodies to use in these assays in order to detect pre-neoplastic and early carcinogenic modifications.

As used herein the terms "cancer-associated marker protein", "cancer-associated protein", "marker protein" or "cancer marker" all refer to cancer-associated modified forms of wild-type proteins.

Cancer markers often differ from the corresponding wild-type proteins in such a way that they are recognised as foreign molecules by the immune system of an individual, triggering an autoimmune-response. The immune-response may be humoral, leading to the production of autoantibodies against the cancer marker protein. Autoantibodies are naturally occurring antibodies directed to an antigen that an individual's immune system recognises as foreign even though that antigen actually originated in that individual. For example, modified forms of p53, MUC-1, c-myc, c-erb3 and Ras proteins may elicit production of autoantibodies. As used herein the term "autoantibody" refers to an antibody directed against a self-originating antigen, which antibody is naturally occurring in the circulation of an individual or to an antibody which exhibits the characteristics of the naturally occurring antibody in that it recognises the said self-originated antigen but which is produced outside the body, for example, by an immortalised cell.

As will be described in the Examples below, the present inventors have surprisingly found that autoantibodies produced by patients suffering from cancer specifically recognise cancer-associated marker proteins from the same patients or from other patients with cancer and show very low cross-reactivity with wild-type forms of these proteins. Furthermore, the present inventors have found that the above autoantibodies have a much higher sensitivity than the antibodies currently used in routine tests and are therefore unable to detect smaller quantities of cancer-associated marker proteins. Autoantibodies produced by patients with cancer may therefore be used to design alternative, more reliable and sensitive tests to detect pre-neoplastic or carcinogenic modifications in an individual from the very beginning of their occurrence. These assays may also be employed to detect cancer or pre-neoplasia in any other mammal, by utilising autoantibodies produced by a mammal from the same species as the one to be tested or autoantibodies having the same characteristics as such.

The present invention provides a more sensitive and specific assay system for the detection of pre-neoplasia or cancer in a mammal, which allows the detection of cancer-associated marker proteins from the early stages of the disease.

Accordingly, in a first aspect the invention provides an in vitro method for detecting a cancer-associated marker protein present in a bodily fluid of a mammal which method comprises the steps of:

(a) contacting a sample of bodily fluid from said mammal wish antibodies directed against at least one epitope of said marker protein; and (b) detecting the presence of any complexes formed between said antibodies and any marker protein present in said sample;

wherein said antibodies are mammalian autoantibodies to said cancer-associated marker protein which are derived from the same species as the mammal from which said sample has been obtained.

The presence of said complexes is indicative of the presence of cancer associated marker proteins in said mammal.

As used herein "derived" means an autoantibody or autoantibodies isolated from the said species or an autoantibody or autoantibodies having the characteristics of an autoantibody or autoantibodies isolated from said species.

The method of the invention may employ a single autoantibody directed against a particular cancer marker protein. Alternatively, a panel of autoantibodies recognising a number of cancer-associated proteins may be utilised in order to obtain a profile of cancer markers present in a particular individual. This leads to a more reliable diagnosis and provides information useful in the choice of the most appropriate treatment for an individual.

The assay method of the invention is performed on a sample of a biological fluid from the patient such as, for example, plasma, serum, whole blood, urine, lymph, faeces, cerebrospinal fluid or nipple aspirate, depending of the nature of the cancer to be detected. Since it is non-invasive the assay can be repeated as often as it is necessary to screen for early neoplastic or carcinogenic modifications, to follow the development of the disease, to test for recurrence of the disease, to verify the efficacy of a treatment or to select the most appropriate treatment for a particular patient.

The method of the invention can be performed using any immunological technique known to those skilled in the art of immunochemistry. As examples, ELISA, radio immunoassays or similar techniques may be utilised. In general, an appropriate autoantibody is immobilised on a solid surface and the sample to be tested is brought into contact with the autoantibody. If the cancer marker protein recognised by the autoantibody is present in the sample, a complex autoantibody-marker is formed. The complex can then be directed or quantitatively measured using, for example, a labelled secondary antibody which specifically recognises an epitope of the marker protein. The secondary antibody may be labelled with biochemical markers such as, for example, horseradish peroxidase (HRP) or alkaline phosphatase (AP), and detection of the complex can be achieved by the addition of a substrate for the enzyme which generates a calorimetric, chemiluminescent or fluorescent product. Alternatively, the presence of the complex may be determined by addition of a marker protein labelled with a detectable label, for example an appropriate enzyme. In this case, the amount of enzymatic activity measured is inversely proportional to the quantity of complex formed and a negative control is needed as a reference to determine the presence of antigen in the sample. Another method for detecting the complex may utilise antibodies or antigens that have been labelled with radioisotopes followed by measure of radioactivity.

The method of the invention can be performed in a qualitative format, which determines the presence or absence of a cancer marker protein in the sample or in a quantitative format, which, in addition, provides a measurement of the quantity of cancer marker protein present in the sample. The quantity of marker protein present in a sample may be calculated utilising any of the above described techniques. In this case, prior to performing the assay, it is necessary to draw a standard curve by measuring the signal obtained, using the same detection reaction that will be used for the assay, from a series of standard samples containing known concentrations of the cancer marker protein. The quantity of cancer marker present in a sample to be screened is then interpolated from the standard curve.

If it is necessary to verify the presence of a number of cancer marker proteins in a sample, the assay of invention may be performed in a multi-well assay plate where each of the different autoantibodies utilised is placed in a different well.

The method of the invention can be employed in a variety of clinical situations such as, for example, in the assessment of the predisposition of an individual towards the development of a cancer, in the detection of pre-neoplastic or carcinogenic modifications in asymptomatic patients, in the diagnosis of primary or secondary cancer, in monitoring the progression of the disease in a patient, in screening for recurrence of carcinogenic modifications in a patient who has previously been diagnosed as carrying cancer cells and has undergone a therapy to reduce the number of these cells or in the choice of the more appropriate anti-cancer treatment for a patient suffering from cancer. The method of the invention is also suitable for veterinary use in the same clinical situations as the ones described above.

The assay method of the invention may be employed to detect cancer marker proteins that are associated with a variety of cancers such as, for example, lymphomas, leukaemia, breast cancers, colorectal cancers, lung cancers, pancreatic cancers, prostate cancers, cervical cancers, ovarian cancers, endometrial cancers and cancers of the skin. The method of the invention is particularly suitable to detect and monitor primary breast cancer (PBC) and advanced breast cancer (ABC).

In a second aspect the invention provides autoantibodies and reagents comprising said autoantibodies for use in the assay, which specifically recognise at least one epitope of a mammalian cancer-associated marker protein. Such autoantibodies may be isolated from the blood or peripheral blood mononucleocytes of such a mammal, preferably a human. Alternatively, the autoantibodies can be produced by immortalised B lymphocytes and directed to an antigen originated in the mammal itself. The reagents comprising autoantibodies according to this aspect of the invention are particularly suitable for use in the detection of mammalian cancer-associated marker proteins in body fluids. Preferred autoantibodies to use in the assay include those against cancer-associated forms of the glycoprotein MUC1 (Batra, S K. et al. (1992) Int J. Pancreatology 12: 271–283), the signal transduction/cell cycle regulatory protein c-myc (Blackwood, E. M. et al. (1994) Molecular Biology of the Cell 5: 597–609), p53 (Matleashewski, G. et al. (1984) EMBO J. 3: 3257–3262), c-erbβ2 (Dsouza, B. et al. (1993) Oncogene 8: 1797–1806) and Ras (Gnudi, L. et al. (1997) Mol. Endocrinol. 11: 67–76).

However, autoantibodies against any other cancer-associated marker protein may be employed in the assay. Particularly suitable for the detection of breast cancers are autoantibodies against a modified MUC1, BRCA1, BRCA2, p53, c-myc, c-erbβ2 or Ras protein associated with primary breast cancer and autoantibodies against a modified MUC1, BRCA1, BRCA2 p53, c-myc, cerbβ2 or Ras protein associated with advanced breast cancer. These autoantibodies are preferably derived from patients diagnosed with the same type of cancer as the one to which these cancer marker protein are associated.

The invention also provides immortalised cell populations capable of producing the above autoantibodies.

The cell populations of the invention may be produced by any method known in the art. As will be described in detail in Example 1 below, B cells from patients diagnosed with cancer may be, for example, immortalised with Epstein Barr Virus. ELISA or any similar techniques may be performed to screen for the production of autoantibodies, utilising marker proteins obtained from a patient affected from cancer which have been immobilised on a solid support.

The invention further provides kits for detecting one or more cancer-associated marker proteins in the biological fluids of a mammal. Such kits include at least mammalian autoantibodies directed against one or more epitopes of a cancer-associated marker protein and means for detecting the formation of complexes between the autoantibodies and the cancer-associated marker protein. Preferably, the autoantibodies are immobilised on a solid surface.

The present invention will be further understood with reference to the following Examples and to the accompanying Figures in which:

FIG. 1 shows the results of an ELISA assay to examine the reactivity of autoantibodies produced by B cells derived from six patients diagnosed with breast cancer (1 to 4, with primary breast cancer, 7 and 11 with advanced breast cancer). For each group of autoantibodies, MUC1 protein purified from the same patient from which the B cells were taken, from other patients or from normal subjects was used as immobilised antigens. The reactivity of mouse monoclonal B55 anti-MUC1 antibody in a parallel assay is included as a comparative control. PBS or antibodies produced by B lymphocytes derived from four healthy subject (N10, N12, N13 and N14) are used as negative controls. MUC1 was eluted from immunoaffinity columns using 0.25 M glycine pH 2.5.

FIG. 2 shows the results of an ELISA assay to assess the reactivity of autoantibodies obtained from B cells derived from patients diagnosed with primary breast cancer with MUC1 protein from different sources. The reactivity of B55 is included as a comparative control. PBS is used as a negative control.

FIG. 4 shows the sequence of the peptide that was used to immunoaffinity-purify MUC1 antibodies from the sera of patients with advanced breast cancer.

Figure 5:
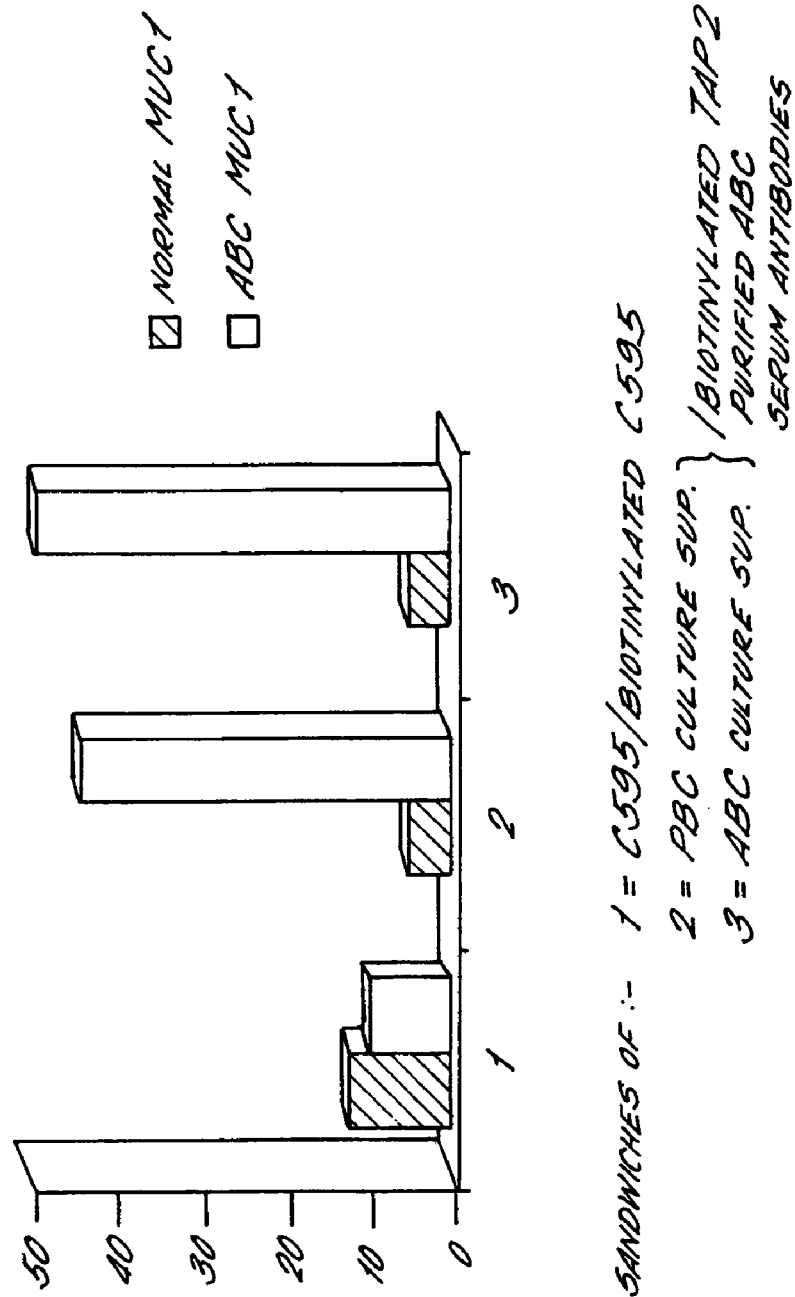

FIG. 5 shows the results of an ELISA assay employing immobilised autoantibodies from a patient with (2) primary breast cancer or (3) advanced breast cancer to detect MUC1 protein purified from the serum of a patient diagnosed with advanced breast cancer or from the urine of a healthy individual. The result of a parallel utilising the anti-MUC1 C595 antibody (1) is included as a comparative example.

Figure 6:
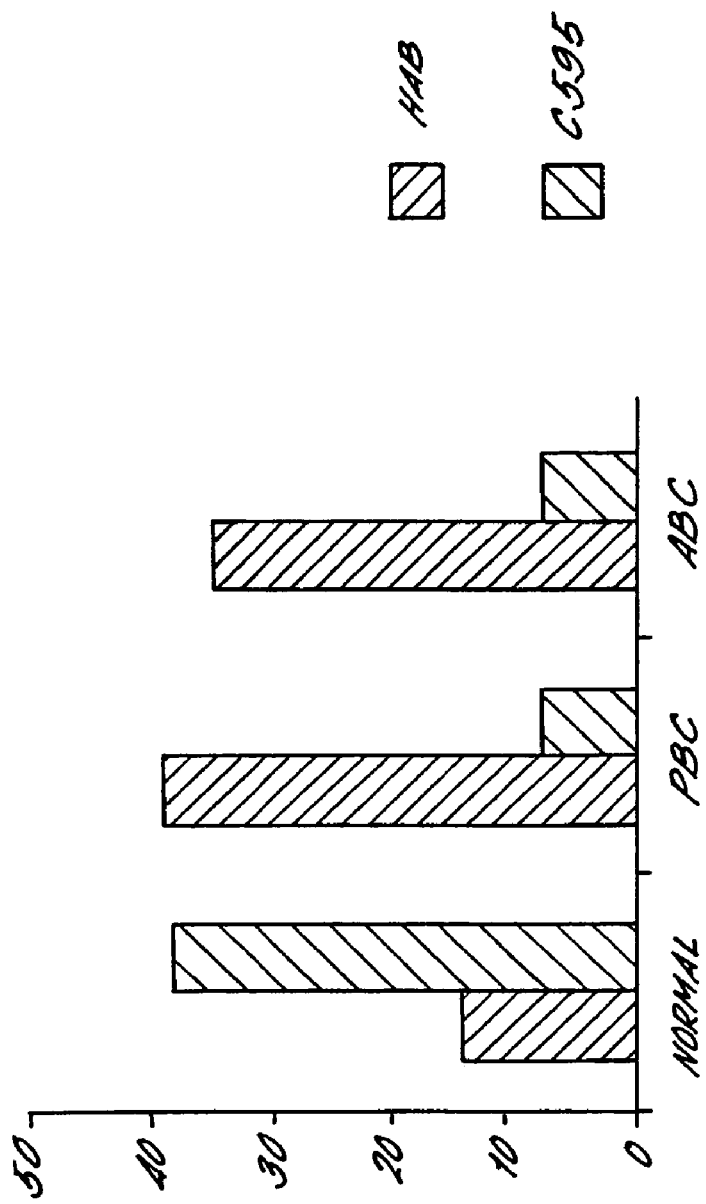

FIG. 6 shows the results of an ELISA assay utilising immobilised autoantibodies from the B cells of patients with primary breast cancer to detect MUC1 protein in serum samples from healthy individuals or from patients diagnosed with primary or advanced breast cancer. The results obtained with the C595 antibody in a parallel assay are included as comparative examples.

Figure 7:
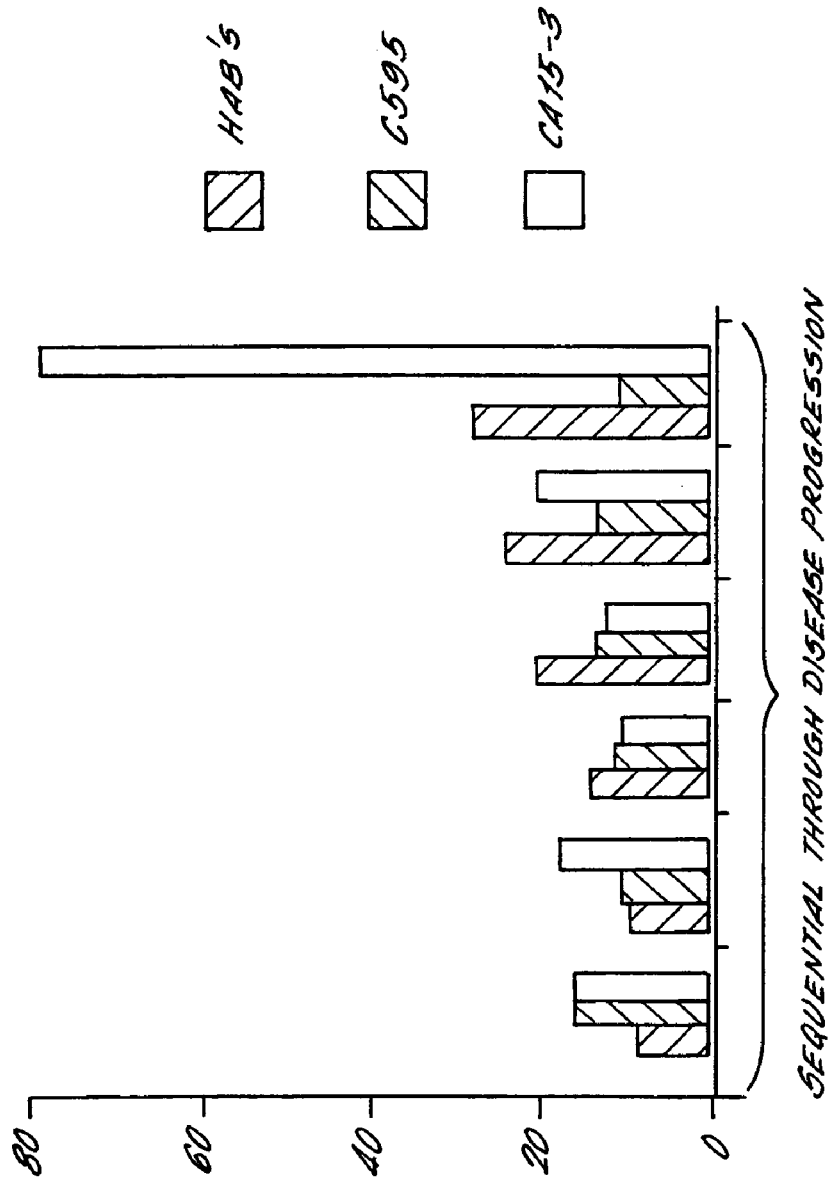

FIG. 7 shows the results of an ELISA assay using immobilised autoantibodies from the B cells of patients with primary breast cancer to detect MUC1 protein in sequential serum samples from a patient with advanced breast cancer throughout the progression of the disease. The results obtained with the monoclonal C595 antibody in a parallel assay or with the commercial CA15-3 assay are included as comparative examples.

Figure 8:
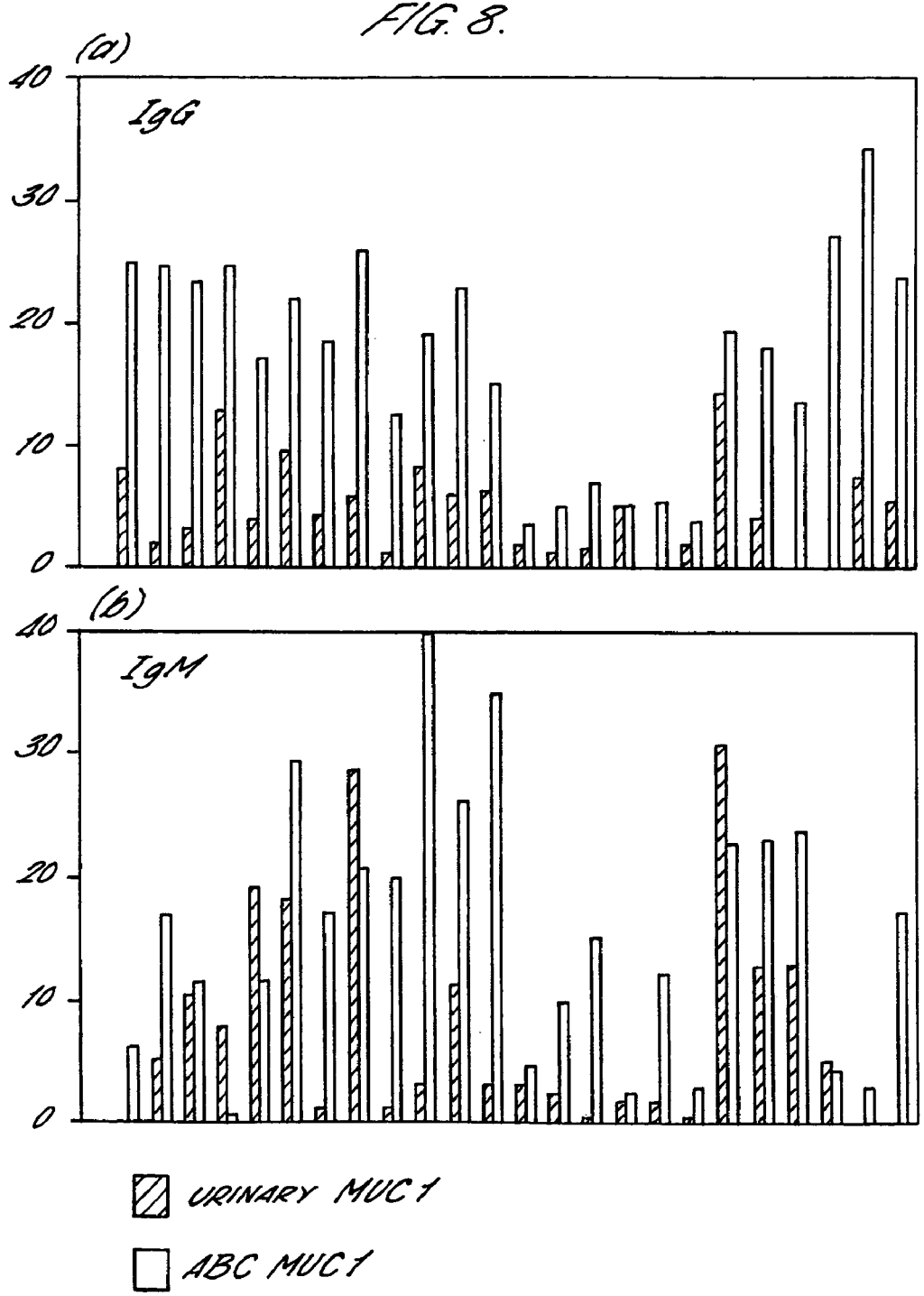

FIG. 8 shows the results of a number of determinations of the reactivity of sera from breast cancer patients with ABC MUC1 and urinary MUC1.

EXAMPLE 1

Immortalisation of Mononucleocytes

Peripheral blood mononucleocytes were purified from a 4 ml sample of heparinised blood from patients or normal individuals using lymphocyte separation medium (ICN flow), as described in detail in the manufacturers instructions. Isolated mononucleocytes were washed in PBS and resuspended in 1 ml of a semipurified preparation of Epstein Barr Virus (EBV) from the B95-8 marmoset transformed leukocyte EBV-producing cell line. The cells were then incubated for 1 hour at 37° C. in 5% $CO_2$ and centrifuged at 17000 rpm. The EBV supernatant was removed and the mononucleocytes were washed three times with RPMI medium, resuspended in RPMI medium supplemented with 10% fetal bovine serum and 5 μg/ml phytoheamatagglutinin (PHA-P) and seeded in multi-wells tissue culture plates. The medium was changed every 3 days and used as a source of autoantibodies.

EXAMPLE 2

Assessment of the Reactivity of Autoantibodies with MUC1 Antigen from Different Sources Methods:

1) Immunoaffinity Purification of MUC1 Antigen

MUC1 was purified from the serum of patients diagnosed with primary breast cancer or advanced breast cancer or from the urine of healthy subjects according to the following protocol.

The mouse monoclonal B55 antibody (also known as NCRC 11 as described by Ellis et al. (1984) Histopathology 8: 501–516 and in International Patent Application No. WO 89/01153) was conjugated to CNBr sepharose beads. Serum or urine samples were diluted 1/10 in PBS and incubated with the antibody conjugated sepharose beads overnight at 4° C. with rolling. The beads were centrifuged and the supernatant removed. In order to remove any molecule non-specifically bound to the beads, these were washed in PBS for 5 times or until the washing buffer showed no absorbance at 280 nm. Each wash was performed by resuspending the beads in PBS, rolling for 10 minutes, centrifuging and removing the supernatant. The washed beads were resuspended in 0.25 M glycine pH 2.5, rolled at room temperature for 10 minutes and centrifuged. The supernatant was removed, adjusted to pH 7 by addition of TRIS and stored at 4° C. labelled "glycine fraction". The beads were then resuspended in 25 mM diethylamine (DEA) pH 11, rolled at room temperature for 10 minutes and centrifuged. The supernatant was again removed, adjusted to pH 7 by addition of TRIS and stored at 4° C. labelled "25 DEA fraction". The beads were finally resuspended in 100 mM DEA pH 11, rolled at room temperature for 10 minutes and centrifuged. The supernatant was removed, adjusted to pH 7 by addition of TRIS and stored at 4° C. labelled "100 DEA fraction". The presence of MUC1 in the three fractions were confirmed by ELISA using the monoclonal antibody B55 or C595 (also known as NCRC, available from the Cancer Research Campaign). In order to remove contaminating immunoglobulins, fractions were incubated with DTT (to 50 mM) for 30 minutes, then iodoacetamide (to 75 mM) before being subjected to gel filtration on a S300 column. Fractions were assayed for MUC1 content by ELISA. MUC1 containing fractions are titrated so as to give equivalent absorbances to previous batches.

2) ELISA Assay

Different MUC1 preparations, obtained as described above, were appropriately diluted with PBS and plated out at 50 µl per well in a 96 well microtitre assay plate and left to dry overnight. The plate was then washed once with PBS/Tween to remove residual salt crystals, blocked for 60 minutes with a fresh solution of 2% (w/v) polyvinylpyrrolidone (PVP) in PBS and washed three times with PBS/Tween. Culture supernatant of immortalised lymphocytes derived from patients diagnosed with primary or secondary breast cancer were plated out in triplicate, at 50 µl per well. As a comparative control the mouse monoclonal anti-MUC1 antibody B55 was also plated in triplicate. The plate was incubated for 60 minutes at room temperature with shaking and washed four times with PNS/Tween. 50 µl of HRP conjugated anti-human or anti-mouse secondary antibody (obtained from Dako) were added to each well at the dilution recommended by the manufacturer, and incubated for 60 minutes at room temperature with shaking. The plate was then washed again four times with PBS/Tween. 50 µl of TetraMethylBenzidine (TMB) were added to each well and optical density (OD) at 650 nm for each well of the assay plate was read kinetically over a period of 10 minutes.

Figure 1:
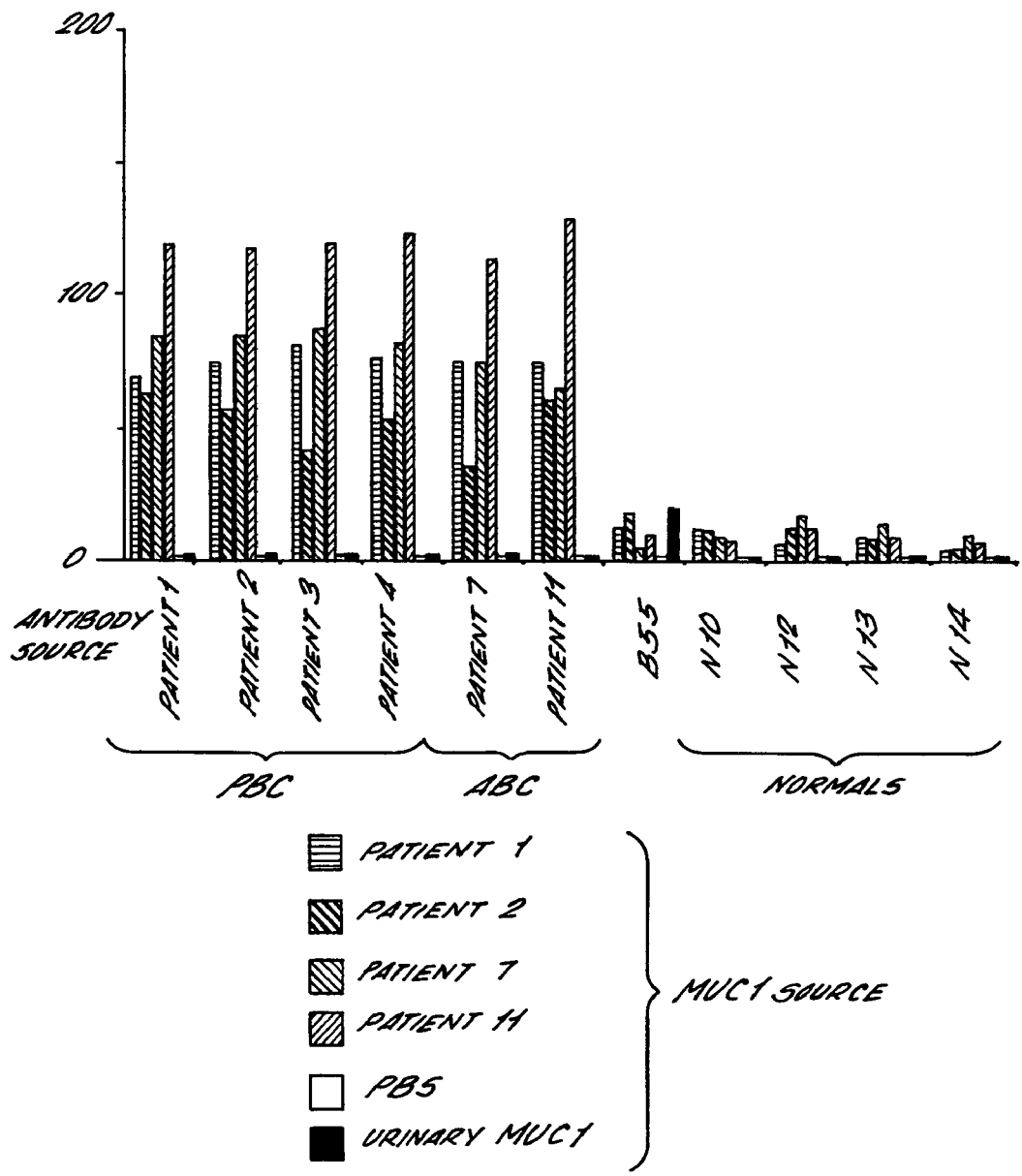

Results:

FIG. 1 shows the result of an ELISA assay to assess the reactivity of autoantibodies produced by lymphocytes derived from six patients diagnosed with breast cancer (1 to 4, with primary breast cancer, 7 and 11 with advanced breast cancer) with MUC1 protein purified from the same patient from which the antibody was taken, from other patients or from healthy subjects. The healthy subjects used in this study were women who had no clinical and/or mammographical evidence of breast cancer. The reactivity of the monoclonal anti-MUC1 B55 antibody was measured as a comparative control. Antibodies produced by lymphocytes from four healthy subjects (N10 to N14) were used as a negative control.

The results presented demonstrate that B lymphocytes derived from patients with breast cancer produce autoantibodies that are able to recognise MUC1 protein isolated both from the same and from different patients. In addition, these autoantibodies bind with high specificity to MUC1 present in patients with cancer, showing almost no reactivity with MUC1 isolated from healthy individuals. These results are highly reproducible, since different autoantibodies show a very similar reactivity profile with MUC1 protein purified from different sources. Furthermore, the results obtained also indicate that the sensitivity of the autoantibodies for cancer-associated MUC1 is much greater than that observed for the monoclonal B55 antibody. Furthermore, antibodies produced by lymphocytes from normal patients did not show this profile.

Figure 2:
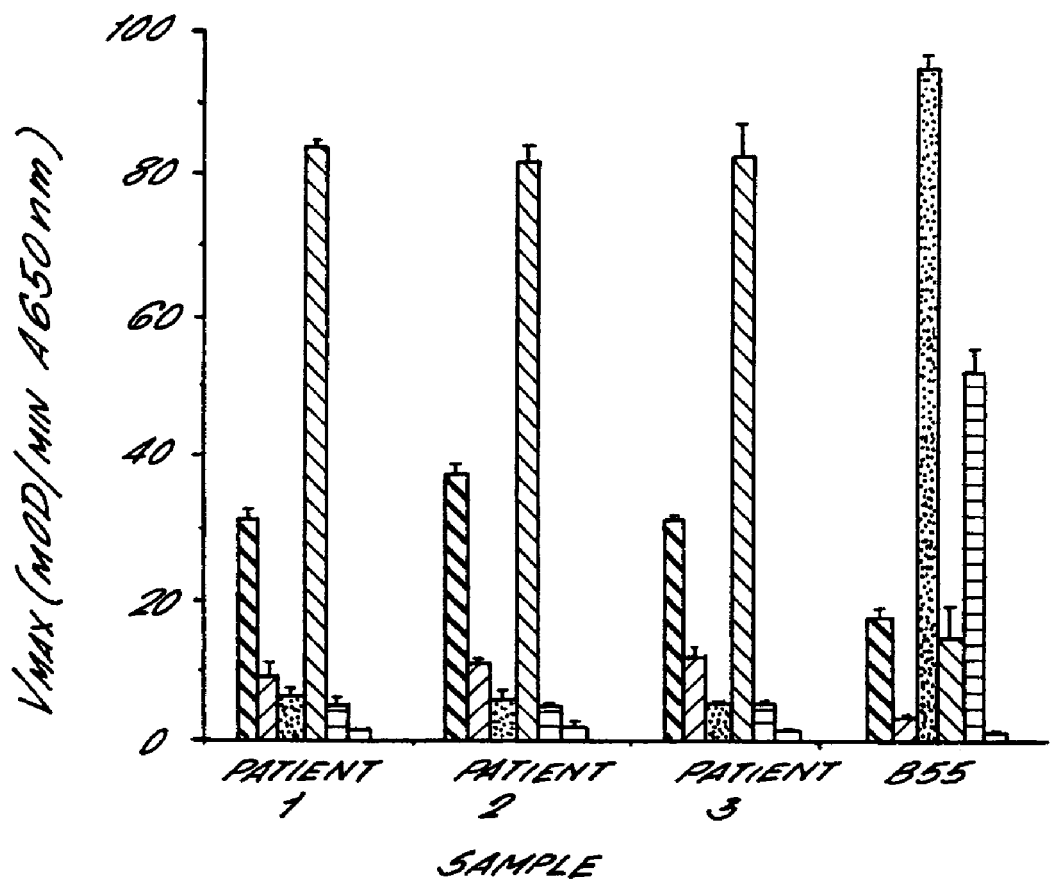

FIG. 2 shows the reactivity of autoantibodies secreted by immortalised B lymphocytes derived from patients with primary breast cancer with MUC1 protein from different sources, compared with that of B55. The profile of reactivity of the different autoantibodies is again very reproducible. The autoantibodies show high specificity for MUC1 present in the serum of patients with cancer and have almost no affinity for MUC1 isolated from healthy individuals or from the breast cancer cell line ZR75-1. Furthermore, the affinity of the autoantibodies for MUC1 protein associated with either primary breast cancer or advanced breast cancer is much higher that measured for B55.

EXAMPLE 3

Measure of the Affinity of Autoantibodies with Surface Plasmon Resonance

Methods

Surface Plasmon Resonance was performed on Iasys Biosensor Plus (from Affinity Sensor). MUC1 protein from patients with advanced breast cancer and from normal individuals were adhered to amino silane coated cells following the manufacturers instructions and the cells were blocked with 1% (w/v) polyvinylpyrrolidone (PVP). Control cells coated only with 1% PVP were also produced. The binding of different dilutions of culture supernatant derived from B cells from patients with primary breast cancer was measured using the following experimental conditions:

| | |
|---|---|
| Sampling interval: | 0.3 msecs |
| Stirrer speed: | 70 rpm |
| Temperature: | 24° C. |
| Binding Time: | 3 min |
| Dissociation with PBS: | 2 minutes |
| Regeneration with 20 mM Hcl: | 3 minutes |
| Re-equilibration with PBS: | 5 minutes |

Results

Figure 3:
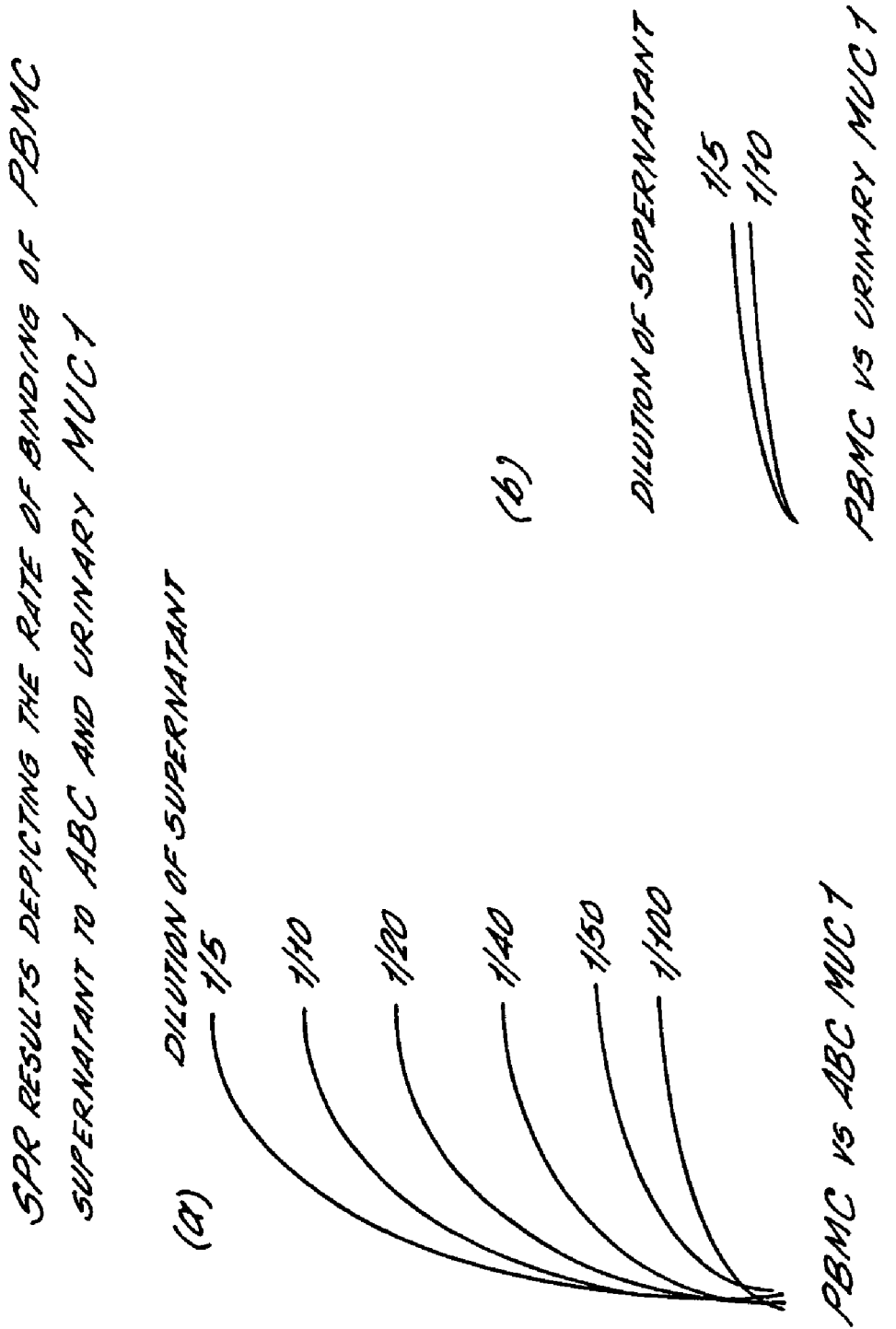
FIG. 3 shows the results of a surface plasmon resonance experiment to measure the binding of autoantibodies produced by B cells derived from patients diagnosed with primary breast cancer to MUC1 protein isolated (a) from the serum of patients with advanced breast cancer or (b) from the urine of normal individuals.

FIG. 3 shows that the autoantibodies produced by B lymphocytes derived from a patient with primary breast cancer bind with a much higher affinity to MUC1 isolated from another patient with breast cancer than MUC1 isolated from a healthy individual.

EXAMPLE 4

Detection of MUC1 Antigen in ELISA Assays Utilising Autoantibodies

Method:

1) Purification of Anti-MUC1 Autoantibodies from Sera

The MUC1 peptide TAP2, with the sequence shown in FIG. 4, was conjugated to CNBr-sepharose beads. Pooled sera from patients diagnosed with advanced breast cancer were diluted 1/10 in PBS and were incubated with the conjugated sepharose beads overnight at 4° C. with rolling (in the ratio of 25 ml of serum to 1 ml of beads). After centrifugation the supernatant was removed and the beads were washed 5 times with PBS or until absorbance at 280 nm was zero. Each wash was performed by resuspending the beads in PBS, rolling for 10 minutes, centrifuging and removing the supernatant. The beads were resuspended in 1 ml of 3M sodium thiocyanate in PBS, rolled at room temperature for 10 minutes and centrifuged. The supernatant was removed and dialysed against PBS at 4° C. The anti-MUC1 content was then confirmed by ELISA using as immobilised antigen both MCU1 isolated from patients with advanced breast cancer and a MUC1 peptide, with sequence APDTRTPAPG and conjugated to BSA.

2) Biotinylation of Anti-MUC1 Autoantibodies

The autoantibodies obtained as described above were concentrated to a volume of 100 µl by using centrifugal filters and then diluted to a volume of 1 ml with 0.1 sodium tetraborate buffer pH 8.8. 20 µg of N-hydroxysuccinimide biotin were added and the autoantibodies/biotin solution was incubated for 4 hours at room temperature with rolling. The reaction was stopped by addition of 10 µl of 1M $NH_4Cl$ and incubation for ten minutes. The autoantibodies were then dialysed against PBS for thirty-six hours at 4° C. to remove unbound biotin. Aliquots of the autoantibodies solution were frozen and stored at −20° C. in the dark until use.

3) ELISA ASSAY

Culture supernatant of lymphocytes derived from patients with primary breast cancer or advanced breast cancer or the monoclonal anti-MUC1 C595 antibody were plated out at 50 µl per well in a 96 well microtitre assay plate and incubated overnight at 4° C. The plate was then washed 4 times with PBS/Tween, blocked for 60 minutes with a fresh solution of 2% (w/v) polyvinylpyrrolidone (PVP) in PBS and washed twice with PBS/Tween. 50 µl per well of MUC1 from different sources were added. After incubation at room temperature for sixty minutes, the plate was washed again four times with PBS/Tween. 50 µl of the appropriate biotinylated secondary antibody, either C595 or autoantibody purified from a pool of sera from a patient with advanced breast cancer, prepared as described above, were added to each well and incubated for 60 minutes at room temperature. After 4 washes with PBS/Tween, 50 µl of streptavidin-HRP were added to each well and incubated at room temperature for 60 minutes. The plate was again washed four times, 50 µl of TMB were added to each well and optical density (OD) at 650 nm for each well of the assay plate was read kinetically over a period of 10 minutes.

Results:

FIG. 5 shows the results of an ELISA assay utilising as immobilised antibodies autoantibodies produced by B lymphocytes derived from patients with primary or advanced breast cancer, compared with those obtained in a parallel assay with the monoclonal anti-MUC1 C595 antibody. The data indicate that autoantibodies from patients with breast cancer can be used in ELISA assays to specifically detect modified forms of MUC1 protein associated with cancer. These assays are more sensitive and show higher specificity than those utilising the monoclonal antibody C595.

EXAMPLE 5

Use of the Assay to Detect MUC1 Proteins in Serum Samples of Patients

An ELISA assay was performed, as described in Example 4, on serum samples from healthy individuals or patients with primary or advanced breast cancer utilising as immobilised antibodies the autoantibodies produced by B lymphocytes derived from patients with primary breast cancer. A parallel assay utilising the monoclonal anti-MUC1 antibody C595 was performed on the same samples. The results, shown in FIG. 6, indicate that the assay employing autoantibodies is able to detect with high sensitivity MUC1 circulating in the blood of patients with breast cancer. In addition, contrary to utilising the monoclonal antibody C595, this assay has a very high specificity for cancer-associated forms of MUC1.

EXAMPLE 6

Use of the Assay to Monitor the Progression of the Disease

An ELISA assay was performed, as described in Example 4, on sequential serum samples from a patient diagnosed with metastatic cancer throughout the progression of the disease, using as immobilised antibodies the autoantibodies produced by B lymphocytes derived from patients with primary breast cancer or the monoclonal anti-MUC1 C595 antibody. The commercial assay CA15-3 was also performed on the same samples. FIG. 7 shows that the assay employing autoantibodies can be used to follow the progression of cancer in a patient, wherein increasing levels of MUC1 detected in the assay indicate exacerbation of the disease. The data also demonstrate that the use of autoantibodies leads to results that better represent the development of the disease than those obtained with either the C959 antibody or the CA15-3 assay.

EXAMPLE 7

Comparison of the Specificity of Anti-MUC1 Autoantibodies to Urinary or ABC MUC1

Method:

Preparations of ABC MUC1 (MUC1 isolated from the serum of patients diagnosed with advanced breast cancer) and urinary MUC1 were prepared as described in Example 2.

Aliquots of the ABC and urinary MUC1 preparations were dried onto the wells microtitre plates separately at concentrations giving equivalent NCRC-11 binding. After blocking with 2% PVP, serum samples taken from patients with breast cancer, diluted 1/100 with PBS, were added to the wells and any anti-MUC1 antibodies in the sera allowed to bind. After washing, the bound antibodies were probed with anti-human IgM-HRP and anti-human IgG-HRP conjugates.

Results

FIG. 8 shows the results of a number of determinations of reactivity of sera from breast cancer patients with ABC and urinary MUC1. Sera from the majority of patients clearly exhibit greater specificity for the ABC MUC1 as compared to urinary MUC1.

The invention claimed is:

1. An in vitro method for detecting a cancer-associated marker protein present in a bodily fluid of a mammal comprising:
   (a) contacting a sample of bodily fluid from said mammal with antibodies directed against at least one epitope of the marker protein; and
   (b) detecting the presence of any complexes formed between said antibodies and the marker protein present in the sample;
   wherein the antibodies are mammalian autoantibodies, which are derived from the same species as the mammal from which the sample has been obtained,
   wherein the sample is from a mammal substantially asymptomatic for pre-neoplasia or cancer, and
   wherein, the cancer-associated marker protein is a modified form of a wild-type protein, and
   wherein detection of the complexes indicates the presence of the cancer-associated marker protein in the bodily fluid.

2. An in vitro method for detecting a cancer-associated marker protein present in a bodily fluid of a mammal comprising:
   (a) contacting a sample of bodily fluid from said mammal with antibodies directed against at least one epitope of the marker protein; and
   (b) detecting the presence of any complexes formed between said antibodies and the marker protein present in the sample;
   wherein the antibodies are mammalian autoantibodies, which are derived from the same species as the mammal from which the sample has been obtained,
   wherein the cancer-associated marker protein is a breast cancer associated marker protein, and
   wherein, the cancer-associated marker protein is a modified form of a wild-type protein, and
   wherein detection of the complexes indicates the presence of the cancer-associated marker protein in the bodily fluid.

3. The method of claim 2 wherein the sample is from a mammal symptomatic for cancer.

4. The method of claim 2 wherein the sample is from a mammal that has received therapy for cancer.

5. The method of claim 1 wherein the mammal is a human and the autoantibodies are human autoantibodies.

6. The method of claim 1 wherein the bodily fluid is plasma, serum, whole blood, urine, feces, lymph, cerebrospinal fluid or nipple aspirate.

7. The method of claim 1 wherein the cancer-associated marker protein is associated with breast cancers, colorectal cancers, lung cancers, pancreatic cancers, prostate cancers, cervical cancers, ovarian cancers, endometrial cancers or cancers of the skin.

8. An in vitro method for detecting a cancer-associated marker protein present in a bodily fluid of a mammal comprising:
   (a) contacting a sample of bodily fluid from said mammal with antibodies directed against at least one epitope of the marker protein; and
   (b) detecting the presence of any complexes formed between said antibodies and the marker protein present in the sample;
   wherein the antibodies are mammalian autoantibodies, which are derived from the same species as the mammal from which the sample has been obtained,
   wherein the cancer-associated marker protein is a modified form of a wild-type MUC1, BRCA1, p53, c-myc, c-erbB2 or Ras protein, and
   wherein detection of the complexes indicates the presence of the cancer-associated marker protein in the bodily fluid.

9. The method of claim 2 wherein the cancer-associated marker protein is a modified MUC1, BRCA1, BRCA2, p53, c-myc, c-erbB2 or Ras protein associated with primary breast cancer.

10. The method of claim 2 wherein the cancer-associated marker protein is a modified MUC1, BRCA1, BRCA2, p53, c-myc, c-erbB2 or Ras protein associated with advanced breast cancer.

11. The method of claim 9 wherein the autoantibodies are obtainable from mononucleocytes isolated from a patient with primary breast cancer.

12. The method of claim 10 wherein the autoantibodies are obtainable from mononucleocytes isolated from a patient with advanced breast cancer.

13. An in vitro method for detecting a cancer-associated marker protein present in a bodily fluid of a mammal comprising:

(a) contacting a sample of bodily fluid from said mammal with antibodies directed against at least one epitope of the marker protein; and
(b) detecting the presence of any complexes formed between said antibodies and the marker protein present in the sample;
wherein the antibodies are mammalian autoantibodies, which are derived from the same species as the mammal from which the sample has been obtained,
wherein the autoantibodies are produced by an immortalized cell or cell population, and
wherein detection of the complexes indicates the presence of the cancer-associated marker protein in the bodily fluid.

14. The method of claim 1 wherein the autoantibodies are polyclonal antibodies.

15. The method of claim 1 wherein the autoantibodies are immobilized on a solid surface.

16. The method of claim 15 wherein any complexes formed between the autoantibodies and any cancer-associated marker protein present in the sample are detected using secondary antibodies or autoantibodies specific for at least one epitope of said marker protein, the secondary autoantibodies carrying a detectable label.

17. The method of claim 15 wherein in addition to the sample a labeled cancer-associated marker protein is added carrying at least one epitope recognized by the autoantibodies.

18. An in vitro method for detecting a breast cancer-associated marker protein present in a bodily fluid of a mammal to screen for recurrence of cancer after a treatment, to monitor systemic therapies or to select therapies comprising:

(a) contacting a sample of bodily fluid from said mammal with antibodies directed against at least one epitope of the marker protein, wherein the antibodies are mammalian autoantibodies to the cancer-associated marker protein and derived from the same species as the mammal from which the sample has been obtained; and (b) detecting the presence of any complexes formed between the antibodies and the marker protein present in the sample;

wherein the cancer-associated marker protein is a modified form of a wild-type protein, and wherein detection of the complexes indicates the presence of the cancer-associated marker protein in the bodily fluid.

* * * * *